(12) United States Patent
Moszner et al.

(10) Patent No.: US 6,939,489 B2
(45) Date of Patent: Sep. 6, 2005

(54) DESKTOP PROCESS FOR PRODUCING DENTAL PRODUCTS BY MEANS OF 3-DIMENSIONAL PLOTTING

(75) Inventors: Norbert Moszner, Eschen (LI); Armin Burgath, Bodmann-Ludwigschafen (DE); Rolf Mulhaupt, Freiburg (DE); Ulrich Salz, Lindau (DE); Volker Rheinberger, Vaduz (LI); Rudiger Landers, Freiburg (DE)

(73) Assignee: Ivoclar Vivadent AG, Schaan (LI)

( * ) Notice: Subject to any disclaimer, the term of this patent is extended or adjusted under 35 U.S.C. 154(b) by 276 days.

(21) Appl. No.: 10/107,526

(22) Filed: Mar. 25, 2002

(65) Prior Publication Data

US 2002/0167100 A1 Nov. 14, 2002

Related U.S. Application Data

(60) Provisional application No. 60/289,922, filed on May 10, 2001.

(30) Foreign Application Priority Data

Mar. 23, 2001 (DE) .......................................... 101 14 290

(51) Int. Cl.[7] .......................... A61C 13/20; B29C 35/08; B29C 41/02; B29C 41/22
(52) U.S. Cl. ........................... 264/16; 264/19; 264/255; 264/298; 264/308; 264/401; 264/494
(58) Field of Search .......................... 264/16, 19, 255, 264/298, 308, 401, 494

(56) References Cited

U.S. PATENT DOCUMENTS

| 5,121,329 | A |   | 6/1992 | Crump |
| 5,348,475 | A | * | 9/1994 | Waknine et al. .......... 264/16 X |
| 5,370,692 | A |   | 12/1994 | Fink et al. |
| 5,768,134 | A |   | 6/1998 | Swaelens et al. |
| 5,894,036 | A | * | 4/1999 | Tylko ..................... 264/401 X |
| 6,096,903 | A |   | 8/2000 | Moszner et al. |

OTHER PUBLICATIONS

Organosilicon Chemistry II, Edited by Norbert Auner & Johann Weis pp. 251–266 & 651–658; publisher VCH Weinhein—New York—Basel Cambridge—Tokyo, undated.

* cited by examiner

Primary Examiner—Leo B. Tentoni
(74) Attorney, Agent, or Firm—John C. Thompson; Alan S. Korman

(57) ABSTRACT

A process for fabricating dental form pieces for dental restoration and replacement parts is provided and includes the step of applying a material, on a firm support or a fluid medium, by a three dimensional plotting technology in a layer by layer manner. The material has micro cords and/or micro drops which include at least one of a meltable, polymerizable, polycondensable, and polyaddable constituent element that is an unfilled monomer, a reinforced monomer, oligomer, polymer, or a ceramic element. The process also includes the step of hardening the applied material by cooling of the material, chemical reaction, polymerization with thermal handling, or polymerization by irradiation of the material with UV or visible light.

35 Claims, 1 Drawing Sheet

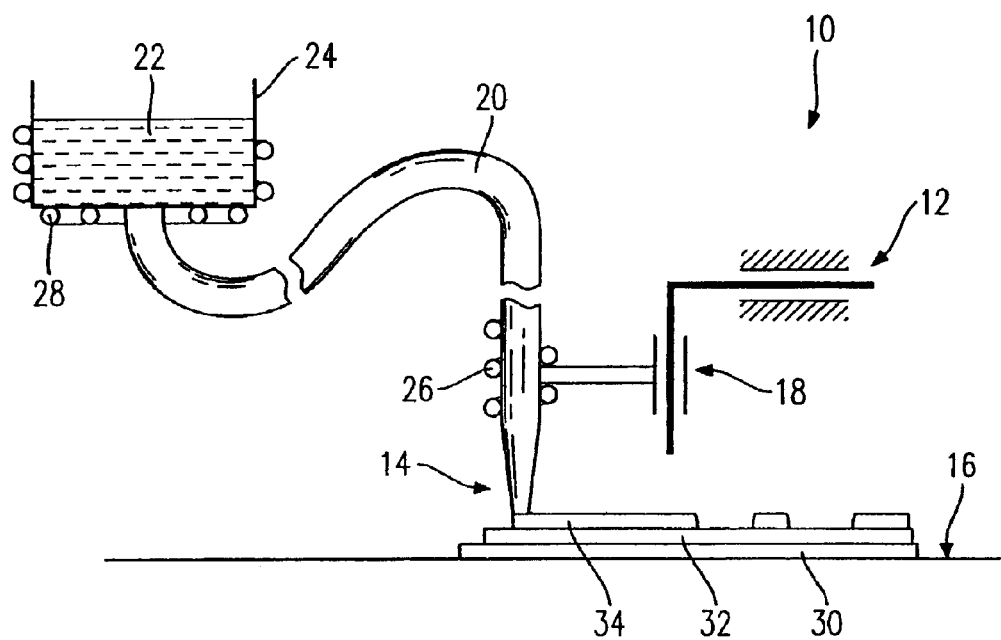

DESKTOP PROCESS FOR PRODUCING DENTAL PRODUCTS BY MEANS OF 3-DIMENSIONAL PLOTTING

This application claims the benefit of Provisional Application No. 60/289,922, filed May 10, 2001.

BACKGROUND OF THE PRESENT INVENTION

The present invention relates to a process using 3-dimensional plotting for producing dental products by which meltable, condensable, thermal or UV or visible light-hardenable unfilled or filled materials are handled by means of a 3-dimensional plotter.

Traditional multiple step molding and casting processes are still overwhelmingly used today for the production of dental replacement products or portions of a dental restoration such as inlays, onlays, bridges, crowns, or prostheses. In this regard, the production of the individual dental form pieces follows in further steps in conventional ways. These conventional processes are proven; however, they require a high degree of effort to produce the finished product. With a view toward ameliorating this effort, a number of processes have been developed, within recent years, with the goal of reducing this effort and improving the quality of the finished products.

In the last several years and, in particular, since 1987, when success was first achieved in generating three dimensional models for a work process directly from a base of computer data, the concept "Rapid Prototyping" has entered the vernacular as a synonym for processes with whose help it is possible to generate, with various accessories or programs, computer data models of varying quality and reliability. In connection with the form or mold free fabrication of items, three dimensional computer pictures are sectioned into layers which are assembled in layer by layer manner, via computer supported fabrication processes, into real three dimensional objects. While the first such models were predominantly demonstration models without any real use potential, models today can, in fact, be fabricated by processes so as to be functional models. Also, small series of items lend themselves to fabrication by these processes. While in the first years of use of such processes, the technically fascinating but cost unfavorable model generating processes predominantly used light hardened acrylic resins (stereolithography), the palette of available materials has clearly grown. Thus, the various processes denominated "Rapid Prototyping" were also implemented in the fabrication of dental products. These principally have comprised selective laser sintering processes, the 3-D printing process, and the stereolithography process.

EP-A-1 021 997 describes the use of a laser sintering process for the fabrication of dental replacement products by which a form body is built of a sinterable powder in a layer by layer manner with each layer being sintered with a laser beam before the application of the following layer. The data needed for controlling the process is data representing the configuration of the form body at each respective layer. An alloy powder in homogeneous form is used as the work material. The disadvantage of this process, however, is that the creation of hollow spaces between the powder material cannot be foreclosed. Moreover, according to the above-noted publication, filled plastic cannot be used as the powder.

WO 97/29901 describes a process (stereolithography) and a device for fabricating three dimensional pieces from a fluid and hardenable medium. In this regard, the piece is built in layer by layer manner with each individual layer being carried off by a laser and thereby hardened. Thereafter, a stripper applies the next layer of the hardenable material and the remaining material is likewise hardened. The publication does not mention the use of materials for dental purposes in its description of the model building process.

U.S. Pat. No. 5,768,134 describes a stereolithographic process for fabricating dental implants. In the disclosed process, a model is generated and modeled in a CAD application; whereby it is known, according to this publication, to use a computer tomography scanned picture for the reconstruction in order to capture the relative position of the prosthetic teeth and the thereunder lying jaw bone and to undertake corrections as needed. As has been noted, this type of process is time consuming while, at the same time, the computer tomography portion is very expensive and is in no way commonly found in dental offices.

There are, moreover, numerous conventional processes by which items can be quickly fabricated based upon models or prototypes. An example of this is described in U.S. Pat. No. 5,370,692. In that disclosed process (modified selective laser sintering), which is heavily weighted toward the replication of bone material in items including thereamong dental implants, the implant layers are built up layer by layer, whereby the application of a layer itself is implemented with a type of pressure on the layer. Ceramic pieces or polymer pieces are preferably bonded with one another in order to build the implant. A pressure application process of this type is, however, not suitable for all circumstances. At the same time, the ceramic cannot, as a rule, be sintered without undergoing a shrinkage process. A further problem in the practical realization of dental prostheses by this process is that a control in the articulator must constantly be performed for the positioning of the tooth. This is accomplished in an intermediate step by the conventional technology involving the creation of a wax prosthesis. It is in practice not possible to remove a model from such a wax prosthesis in a disturbance-free manner since, at the least, micro back cuts occur and a wax model material typically exhibits, even at room temperature, a reduced hardness relative to, for example, plaster.

DE 196 42 247 describes a process for fabricating dental replacement products in which, initially, three dimensional product data is captured and prepared for the fabrication of the dental replacement product. In this process, a computer controlled machine tool is used to ensure the fast production of a prototype based upon the basic product data. Although this process admittedly enables a decidedly exact fabrication of the dental replacement product, the fabrication process requires significant resources and requires an electronically controllable machine tool, which performs the desired work by means of a cutting process. This process suffers from a number of disadvantages, however, in that remnants and debris are created which cannot be tolerated in a dental office practice. Moreover, the thus fabricated dental replacement product must frequently be coated by conventional processes, as the material produced does not meet the aesthetic requirements for such dental replacement products.

It is further conventionally known to use a three dimensional pressure technology for the fast fabrication of prototypes. In this regard, two processes are used: in one process (3-D printing), which has been developed by Massachusetts Institute of Technology, a material in powder form is supplied with a binder material via a spray device in a layer by layer manner to form a shape corresponding to the object to be fabricated and the binder material binds the newly applied powder material to the already applied layers. In this process, the excess non-bound powder material is removed in the finishing of the object. The use of powder material provides design freedom in fabricating an object by this process, whereby nonetheless the object is frequently left with a gritty or granular surface and hollow spaces, which can impact the firmness of the object, cannot be precluded. Follow up handling is typically required to increase the mechanical integrity and the outer surface of the object. In another conventional process (fused deposition modeling), a three dimensional pressure technology is used in connection with electrostatic ink spray nozzles to apply a material hardenable by contact with air. This material is melted and then flowed through the nozzles to be applied thereby. Due to the need to effect a complete through hardening of the material, it is necessary to use significantly small material pieces, whereby the fabrication process takes a correspondingly long time. Typically, a material cord is melted in a 3-D dimensionable nozzle and applied thereby. In this regard, however, the choice of suitable materials is limited to only a few thermoplastic materials such as, for example, ABS. A further disadvantage is that a cord of suitable dimension of the material to be applied must first be produced which can then be subsequently applied through the nozzle.

It is further known to fabricate computer supported three dimensional objects, whereby the three dimensional structure is constructed in layer by layer manner by the addition of micro points or micro cords in a fluid medium (Macromolecular Materials and Engineering 2000, 282, pages 17–21). By this process, it is possible to construct structures from mechanically unstable materials, which, in compensating for gravity by passage in the fluid medium, maintain their geometry after the build up of the structure up to mechanical or chemical consolidation. This process allows in this manner the use of materials, which were heretofore not suitable for a Rapid Prototyping process. The use of this process for the fabrication of dental products is, however, not described in the prior art.

SUMMARY OF THE INVENTION

The present invention offers a solution to the challenge of providing a process for the fabrication of dental products with the use of 3-dimensional plotting such that the fabrication of various types of structured form pieces, out of various materials, is possible and only a low investment cost is required.

The process of the present invention with the use of 3-dimensional plotting allows the production of dental products on the basis of meltable, condensable, thermal or UV or visible light-hardenable unfilled or filled materials, which are handled by means of a 3-dimensional plotter. It is for the first time possible, with the process of the present invention, to fabricate dental materials on the basis of high viscosity or, respectively, filled, intermediate production materials via a computer supported form or mold free finishing process. This thus permits the construction of 3-D objects in layered manner through a computer controlled cutting away of micro drops or micro cords in a fluid medium or on a firm oversurface. The hardening of the material follows as a function of the material used in the building of the dental object, either through cooling of the melted material, chemical reaction, or polymerization with thermal or, respectively, simultaneous, or thereafter following, irradiation. It is, moreover, possible to effect a complete hardening of the material through a chemical reaction with a fluid medium.

The application of the material is effected via pneumatic supply with the use of commercially available one way nozzles having a nozzle opening of between about 100 to 2000 $\mu$m, whereby the diameter of the nozzle opening and the pressure of the forced air is dependent upon the viscosity of the material. Moreover, double cartridges are available in connection with two component materials. Dose adjustable cartridges or several cartridges can be exchanged in the course of the material supply. While only thin fluid elements or, respectively, element mixtures can be worked with a binder material in connection with 3-D printing, high viscosity and filled material elements and material element mixtures of the type which find use in important dental products such as, for example, artificial teeth, filling material, or blended or support materials, can be used in connection with 3-dimensional plotting. Known CNC processes such as, for example, those for the cutting away of metal, can be used to control the 3-dimensional plotting processes, whereby the base data is accessible via 3-D scanners, 3-D digital photography, or, as well, via the picture generating process known in the medical arts.

In contrast to the current "Rapid Prototyping" process, the process of the present invention permits the fabrication of widely varied structured form pieces. Besides homogeneously constructed pieces, it is also possible to build in a simple manner porous form pieces or form pieces comprised of different layers to correspond with a gradient sample. At the same time, gradients can be produced via variation of the materials in the course of the plotting. The 3-dimensional plotting accordingly permits, in contrast to the current and known "Rapid Prototyping" process, the building, from composition bases, of artificial teeth or inlays with layered structure, glass reinforced crowns- and bridge-supports or ceramic core bodies for dental purposes. Moreover, the 3-dimensional plotting apparatus is significantly less resource demanding than the known processes.

In contrast to the known processes, the use of the 3-dimensional plotting initially permits greater layer strength, which is produced by the point- or, respectively, the cord-form application of the unfilled or filled materials. In this manner, there is a combining together of the chemical reactive systems of at least two components which had been mixed together immediately before their application onto the object being built up and which react immediately after this application—that is, they harden and form a stable layer. Light-hardenable materials typically comprise a photo initiator. After the application of the layers, there follows an irradiation of these layers with light of a wavelength selected to effect activation of the photo initiator and thus the consequent hardening of the materials. In contrast to those materials having such photo initiators, the ceramic systems, due to their thixotrophy, have sufficient cohesiveness to allow one to omit an intermediate hardening of the individual layers.

These factors permit the realization of a cost favorable plot implementation, whereby, in accordance with the present invention, a nozzle, whose operation can be computer controlled, can apply a micro cord or micro drops. The diameter of the nozzle can thus, in total, have a value up to 2 mm so that a fast application of the layers in the desired form can be realized. A fast build up of the dental products is possible due to the high material strength.

In accordance with the present invention, it is particularly advantageous that pieces for the dental replacement products can be fabricated based on meltable, condensable, thermal or UV or visible light-hardenable unfilled or filled materials which are handled by means of a 3-dimensional plotter. It is especially preferred that the build up of the 3-D object be performed in a layer by layer manner by cutting away microdrops or micro cords in a fluid medium or, alternatively, drying the same on a firm oversurface. The hardening of the materials follows, as a function of the type of material, through cooling of melted material, polycondensation or, respectively, polyaddition, or by the initiation of polymerization in a thermal manner or, alternately, simultaneously with, or subsequently by, an irradiation of the material. A complete hardening of the material through chemical reaction with a fluid medium is also possible.

It is also possible to use commercially available one-way dosing devices which comprise a nozzle opening of from 200 to 2000 micrometers, whereby the diameter of the nozzle opening or, respectively, the pressure to be exerted for the application of the material, is dependent upon the viscosity of the material selected for use. In this regard, it is to understood that, instead of a single nozzle, a plurality of nozzles may be deployed to apply various materials. The dose administration of the material is preferably effected by a pressurized air impact from the one-way dosing device.

Alternatively, a double cartridge or other multiple cartridge dosing device can be deployed, which can even provide the capability to apply materials comprised of two components which are mixed together during their passage through the dosing device and which harden after their application.

In the event that light-hardenable materials are used, conventional light sources are deployed, whereby it is preferred that a UV component be provided within the deployed light spectrum.

In accordance with the present invention, a further advantageous aspect resides in the fact that the process of the present invention can be performed directly at dental practice offices.

In accordance with an advantageous embodiment of the process of the present invention, it is provided that the build up of the layers to form the dental product is performed according to the natural pattern of, for example, a tooth. The dental replacement product frequently has a plastic or ceramic material similar to that of a natural tooth which material corresponds to the tooth bloom but, also, the dental replacement product comprises plastic or ceramic material which corresponds to the dentin. Additionally, there is sometimes a need to use an opaque material for the purpose, for example, of color blending.

In an advantageous embodiment of the process of the present invention, the translucent characteristic of the respective applied layer is accommodated to the required translucent characteristic of the dental replacement product being fabricated. If, for example, the labial side of a front tooth were to be modeled, the arrangement of the build up of the layers is preferably performed such that the labial finishing layer of the front dental replacement product is applied as the last layer.

In a particularly advantageous embodiment of the process of the present invention, materials or combinations of materials are selected which exert a bioactive and/or medicinal effect by, for example, releasing fluoride, hydroxide or calcium ions. Moreover, it is possible to use materials which reduce the retention of plaque thereon or which exhibit a good characteristic for polishing for the fabrication of aesthetic oversurfaces. In connection with the use of ceramic paste, core bodies can be fabricated which are then subsequently hardened using conventional techniques.

BRIEF DESCRIPTION OF THE DRAWING

An embodiment of the invention is shown somewhat schematically in the attached drawing comprising one FIGURE.

DETAILED DESCRIPTION

In the drawing, a conventional 3-D plotter is shown which has the usual XY-drive means 12 for moving a plot nozzle 14 all over a support 16. In usual plotters, this is a piece of paper or cardboard for plotting.

The invention improves this plotter by adding the third dimension such that the inventive plotter is a 3-D plotter 10. Thus, a third axis, the Z-axis, is added, and a Z-drive means 18 is shown schematically in the FIGURE.

The plot nozzle 14 is connected to a tube 20 which receives a fluid 22 from a container 24. The fluid 22 may be a polymerizable fluid. The present invention adds a heating means. Thus, the plot nozzle 14 is heated at its periphery and the tube 20 may also be heated such that it heats the fluid 22 contained in the tube 20 and nozzle 14. The heat may be achieved by a spirally wound wire 26, which heats when supplied with electric current. Likewise, the container 24 may be heated by a wire 28 such that it heats the fluid 22 contained in the container 24. Alternatively, small tubes of hot water may be used for heating.

Preferably, the temperature in the container 24 is set such that the polymerization of fluid 22 is not initiated. According to a preferred embodiment, the temperature is higher in plot nozzle 14 such that the polymerization of fluid 22 is supported.

Preferably, however, the polymerization is a light polymerization and the support 16 is moved towards a light source to enable the polymerization.

In the FIGURE, three layers 30, 32, and 34 of the supplied fluid are shown. Layer 30 is hardened to a viscosity which allows the application of layer 32, before layer 32 is applied. It is also possible to arrange a further—not shown—heating means under support 16 to allow curing of the layers before application of the next layer.

According to the invention, it is sufficient to have layer 30 cured to a semi-hardened state while the final hardness may be achieved after all layers 30 to 34 are applied.

As may be taken from the drawing, layer 34 is applied intermittently such that the desired form may be achieved.

It is to be understood that the layers are rather slim and a plurality of layers is used for 3=D plotting while the drawing only shows three thick layers, for the ease of understandability.

The examples that follow are intended to clarify the present invention but no claim is made as to completeness. In the execution of all of the examples, a 3-D plotter available from Envision Technologies GmbH of Marl, Germany, was used, which plotter is shown in DE 100 18 987. The nozzle diameter of the computer controlled plotter unit was for all examples 200 $\mu$m. Insofar as not otherwise indicated, all of the examples were plotted in air without the use of a reactive medium. The examples demonstrate the use of conventional dental type restoration materials for the fabrication of an inlay. In this connection, a cavity in a tooth was prepared and the cavity was measured by a conventional scanner system. The finishing of the inlay was subsequently performed with the data acquired in this manner, as is hereinafter described.

EXAMPLES

Example 1

Treatment to Completion of an Inlay Comprised of a Light Hardenable, Low Viscosity Dental-Like Filling Material The inlay was fabricated with a conventional low viscosity, light hardenable film (Tetric Flow available from Ivoclar-Vivadent AG). To fabricate the inlay, data concerning the cavity was transferred into the computer controlled plotting unit. The fabrication of the inlay then followed by computer controlled cutting away of micro points of the material disposed on a metal oversurface. The hardening of the deployed materials was accomplished by a light source disposed parallel to the nozzle emitting light in a wavelength range of 400 to 500 nm. The construction of the cavity was conducted in a manner such that a micro point was plotted every 10 seconds. In the interval between the plots of every two successive points, the outlet opening of the nozzle was closed and the above-noted light source was activated to effect the hardening.

Example 2

The fabrication of the inlay of Example 1 above was repeated with the use of another conventional dental like film (Heliomolar Flow, Tetra Chroma and Ariston AT available from Ivoclar-Vivadent AG).

Example 3

The Fabrication of an Inlay Comprised of a Light Hardenable, Short Length Glass Fiber Filled Monomer Mixture A short length glass fiber filled monomer mixture combined in the hereafter described combination was used to fabricate the inlay. The following data is given as percent by weight.

30% short length glass fibers (fabricated by Schott) having an average length of 115 mm
29% Bisphenol—A—Diglycidyldimethacrylate (Bis-GMA)
26% 7,7,9-Trimethyl-4,13-dioxo-3,14-dioxa-5,12-diazahexadecane-I,16-dioxy-di-methacrylate
14% Triethyleneglycoldimethacrylate
1% low molecular stabilizers, additives, and initiators The fabrication of the short length glass fiber filled monomer mixture included a working in of the short length glass fibers into the monomer mixture by means of a moving tool.

The inlay was thereafter constructed by use of the computer controlled plotting unit to conduct a computer controlled cutting away of micro cords of the selected material which had been disposed on a metal oversurface. The hardening of the selected material was accomplished by a light source disposed parallel to the nozzle emitting light in the wavelength range of 400 to 500 nm. In this connection, the light source was mounted on the side of the nozzle which itself was formed of a non-light transmitting material. This arrangement made it possible to perform a simultaneous cutting away and hardening of the selected material.

Example 4

The Fabrication of an Inlay Comprised a Dual Hardenable Dental Like Film (That is—a Dental Like Film Hardened by Both a Self-Hardening Process and by a Light Irradiation Process)

A conventional dual hardenable film (Variolink II Base and Cat available from Ivoclar-Vivadent AG) was used to fabricate the inlay. To fabricate the inlay, data relating to the cavity was transferred to the computer controlled plotter unit. The fabrication of the inlay then followed by computer controlled cutting away of micro points of the selected material which had been disposed on a metal oversurface. In this connection, a mixing container was used which permitted the two components Variolink II Base and Variolink II Cat, to first be mixed in equal portions immediately before the nozzle outlet. The hardening of the selected materials then followed in a self-hardening manner. The fabrication of the cavity then continued in a manner such that a micro point was plotted every 30 seconds.

Example 5

The fabrication of an inlay in the manner described in Example 4 was performed with the addition of a light source disposed parallel to the nozzle emitting light in the wavelength range of 400 to 500 nm. The nozzle outlet opening was covered during the intervals between the plotting of the micro points.

Example 6

The fabrication of an inlay in the manner describe in Example 4 was performed with the use of a second nozzle. Each of the two nozzles was provided with a separate material supply receptacle. One of the nozzle material supply receptacles was filled with Variolink II Base while the other nozzle material supply receptacle was filled with Variolink II Cat. The outlet openings of the two nozzles were configured such that a mixing of the two supplied materials first occurred following their passage beyond the nozzles. In order to ensure a sufficient time interval for the self hardening process of the selected materials, the time interval between the plotting of each respective consecutive pair of points was increased to 60 seconds. The use, in the alternative, of the light source described in Example 5 could reduce the hardening time to 10 seconds.

Example 7

Coating of a Metallic Test Body with a Ceramic Glaze Paste

A coating of a metallic test body with a conventional ceramic precursor (such as, for example, IPS-Empress available from Ivoclar-Vivadent AG) was performed by means of a point by point application of the ceramic precursor on a metallic test body with the 3-D plotter which was used in connection with the above-noted Examples 1–4. A hardening of the applied coating was performed after the plotting process in a commercial oven (Programat by Ivoclar-Vivadent AG).

The scanning of the metallic test body was accomplished with a conventional scanner system. The scanning data was then transferred to the computer controlled plotter unit.

Example 8

The metallic ceramic combination fabricated by the process described in Example 7 was optically scanned in the manner described in Example 7 and coated with a conventional glaze paste (such as, for example, IPS-Empress glaze paste available from Ivoclar-Vivadent AG). This coating is applied in a cord application of the glaze paste in a like manner to that of the material applications described in the preceding examples. A hardening of the applied layers was performed in a commercial oven (Programat by Ivoclar-Vivadent AG) following the plotting process.

Materials

Pure combinations or mixtures of polyreactive monomers, oligomers or polymers, which preferably include suitable fillers and additional additives, can be used as polymer material. In this regard, the following can be considered as matrix systems:

A. Polymerizable Matrix Systems—Examples of these include:
1. Radical polymerizable material having a base of radical polymerizable monomers, such as (meth) acrylate, styrene, and styrene derivate, allyl connectors or vinylcyclopropane, whereby, above all, (meth)acrylate is particularly suitable. Commercially available monofunctional monomers such as, for example, methyl-, ethyl, butyl-, benzyl-, furfuryl- or phenyl (meth) acrylate and the known bindable monomer multifunctionl acrylate or, respectively, methacrylate such as, for example, bisphenol-A-di(meth) acrylate, Bis-GMA (an additive product of methacryl acid and bisphenol-A-diglyoidylether), UDMA (an additive product of 2-hydroxyethylmethacrylate and 2,2,4-hexamethylenediisocyanate), di-, tri-, or tetra-ethyleneglycoldi(meth)acrylate, polyethyleneglycoldimethacrylate, trimethylolpropanetri (meth) acrylate, pentaerythrittetra (meth)acrylate as well as butanedioldi (meth)acrylate, 1,10-decanedioldi(meth) acrylate or 1,12-dodecanedioldi(meth)acrylate.
2. Radical polymerizable oligomers or polymers, which carry end constant and/or side constant radical polymerizable groups, for example, radical polymerizable a, (5 Mw) 10U (meth)acryloyl-terminated polyester-, polyether-, polyepoxide-amine- or polyurethane-telechele or pebble acid polycondensate, which, for example, are introduced by hydrolytic condensation of silanen, which carry radical polymerizable groups of, preferably, for example, methacrylate- or acrylic groups. Such pebble acid polycondensates are described, for example, in DE-PS 4 416 857 or DE-PS 4 133 494.

The complete hardening of the radical polymerizable elements occurs, following the addition of suitable initiators, by thermal, photochemical, or redox-induced polymerization. To initiate the radical polymerization, thermal and/or photo initiators are preferably introduced. Preferred examples of thermal initiators are the known peroxides such as, for example, dibenzoylperoxide, dilsurylperoxide, tert.-butylperoctoate or tert.-butylperbenzoate as well as other azobisisobutyroethylester, azobisisobutyronitril, benzpinakol or 2,2-dimethylbenzpinakol. Examples of suitable photo initiators are benzopheneon, benzoin as well as its derivatives, or a-diketone or its derivative such as 9,10-phenanthrenchinon, diacetyl or 4,4-dichlorbenzil. Campherchinon and 2,2-Methoxy-2-phenyl-acetophenone are particularly preferred and a-diketone in combination with aminen is particularly preferred as a reducing means with, for example, 4-(N,N-dimethylamino)-benzo acid ester, N,N-dimethylaminoethylmethacrylate, N,N-dimethyl-sym-xylidin or triethanolamine. Moreover, acylphosphine such as, for example, 2,4,6-trimethylbensoyldiphenyl- or Bis(2, 6dichlorbenzoyl)-4-N-propylhenylphosphinoxide are particularly preferred.

As initiators for a polymerization conducted at room temperature, redox-initiator combinations such as, for example, combinations of benzoyl- or laurylperoxide with N,N-dimethyl-sym.-xylidin or N,N-dimethyl-p-toluidine, are used.

3. Cationic polymerizable thinner or binder monomers such as, for example, glycidylether or cycloaliphatic epoxide, cyclic katenacetale, vinylether, spiroorthocarbonate, oxetane or bicyclic orthoester. Examples are: triethylanglycoldivinylether, cyclohexandimethanoldivinylether, 2-methylen-1,4,6-trioxaspiro[2.2]-nonan, 3,9-dimethylen-1,5,7,11-tetraoxaspiro[5.5]undecan, 2-methylen-1,3-dioxepan, 2-phenyl-4-methylene-1,3-dioxolane, bisphenol-a-diglycidylether, 3,4-epoxycyclohexylmethyl-3,4-epoxycyclohexancarboxylate, Bis(-(3,4-epoxycyclohexylmethyl)adipate, vinylcyclohexendioxide, 3-ethyl-3-hydroxymethyloxetane, 1,10,-decandiylbis (oxymethylene) bis (3-ethyloxetane) or 3,3-(4-xylylendioxy)-bis-(methyl-3-ethyloxetane). For cationic polymerizable matrix systems, pebble durepolycondensate is suitable, which, for example, through hydrolytic condensation of silanen, carries the cationic polymerizable group preferably comprising, for example, epoxide-, oxetane-, spiroorthoester or vinylether groups. Such pebble acid polycondensates are described, for example, in DE-PS 4 133 494 or U.S. Pat. No. 6,096,903.

Particularly suitable for the complete hardening of cationic polymerizable systems are diaryliodonium or triarylsulfonium salt such as, for example, triphenylsulfonium-hexafluorophosphate or hexafluoroantimonate or, respectively, the systems described in WO 97/13538 or WO 98/47046.

4. Also, materials based upon the mixing of radical and cationic polymerizable connectors, along with suitable initiator combinations, can be introduced, whereby the radical cationic polymerization occurs at the same time or in successive stages.
5. Cyclic monomers which bind by the action of ring-opening metathesepolymerization (ROMP), such as monocyclic alkene or alkadiene such as, for example, cyclopentene, cycloheptane, cyclooctene, cyclododecene or 1,5-cyclooctadiene, or bicyclic alkene such as, for example, bicyclo[2.2.1]hept-2-ene (2-norbornene) or, respectively, derivatives therefrom such as 7-oxa-bicyclo [2.2.1] hept-2-ene, bicyclo[2.2.1] hept-5-ene-2,3-dicarbonaciddimethylester, 7-oxabicyclo[2.2.1] hept-5-ene-2,3-dicarbonaciddiethylester, 5-norbornene-2-methylester or, respectively, 5-norbornene-2-yl-ester from mono-, di-, and multi-carbon acids or the reaction products from 5-norbornene-2-methanol or respectively 5-norbornene-2-ol with mono- or di-isocyanates are introduced. In this regard, polymer networks are formed from such connections which comprise several norbornene groups. For complete hardening, conventional ROMP-catalyzers such as metal carbon complexes such as, for example, Ru-, W-, or Mo-carbon complexes (compare R. R. Schrock, Acc. Chem. Res. 23 (1990) 158) or simple salts such as $K_2RuCl_5$ or hydrates of $RuCl_3$ or $O_sCl_3$ with polar monomers (W. J. Feast, D. B. Harrison, Polymer 32 (1991) 558) can be introduced: moreover, particularly suitable are air- or water-stable catalyzers based on carbonyl groups containing Mo-, Ru-, $O_s$—, or W-connectors with polyeneligands (WO 93/13171) such as, for example, $[(C_6H_6)Ru\ (CH_3CN)_2CI]^+PF_6^-$ or, as photoinitiators, photostable Ru— or $O_s$ connectors such as, for example, $[O_s(C_6H_6)CI_2]_2$ or $[Ru(C_6H_6)]_2$ (Tosylate)$_2$.

B. Polyadditions-Matrix Systems—Examples of these include:
1. Polyurethane or, respectively, polyurea systems: Conventional polyurethane formed of mixtures of commercially accessible diisocyanate such as, for example, toluelenediisocyanate, methylenediphenyldiisocyanate, 2,2,4-trimethylhexamethylenediiso-cyanate or isophoronediisocyanate, or, respectively, oligomer polyisocyanates produced therefrom and having suitable OH-multifunctional connections such as ethyleneglycol, glycerin, or trimethylolpropane or, respectively, di- or tri-functional polyolen produced therefrom, whereby tin organic connections or tertiary amines are introduced as catalyzers. If the isocyanates with diamine, such as, for example, ethylenediamine, hexamethylenediamine or bis (4-amino-3-methylcyclohexyl)methane are reacted, corresponding polyurea elements result therefrom.

2. Epoxide resin: polyadduct from conventional di- or multifunctional epoxide connectors such as, for example, tetrahydrophthalaciddiglyciddylester, bisphenol-A-diglycidylether, hydrogenated bisphenol-A-diglycidylether, glycerintriglycidylether, 3,4-epoxycyclohexylmethyl-3,4-epoxycyclohexanecarboxylate or bis-3,4-epoxycyclohexylmethyl)—adipate with di- or polyamines such as ethylenediamine, triethylenetetramine, diaminocyclohexane, tricyclodecandiamine, hexamethylenediamine or mxylylenediamine or, respectively, polyetherpolyamines. Moreover, anhydrides can be considered as binders.

3. Thiol—en systems: reaction products from di- or multifunctional SH compounds such as, for example, 1,4 dimercaptobenzene, trimethylolpropane-tris(3-mercaptopropionate) or pentaerythrititetrakis (3-mercaptopropionate) with, for example, diallylether, triallylisocyanurate or reaction products from 5-norbornene-2-methanol or, respectively, 5-norbornene-2-ol with diisocyanates. In this connection, the thiol-en polyaddition can be released by conventional radical initiators such as, for example, azobisisobutyronitril.

4. Michael reactions resins: Examples of these include reaction products from di- or multi-functional acrylates with di- or multi-functional acetoacetates. Examples for suitable acrylates are ethyleneglycoldiacrylate, hexanediolacrylate, tripropylene-glycoldiacrylate, ethoxylated bisphenol-A-diacrylate, polyethyleneglycol-200-diacrylate, trimethylolpropantriacrylate, pentaerythritetraacrylate. The acrylates are transformable into network polymers by combination with, especially, tri- or tetra-functional acetoacetates such as, for example, trimethylolprane- and glycerintrisacetoacetate as well as pentaerythrittetrakis-acetoacetate. Suitable catalyzers are preferably alkali metal hydroxide such as, for example, KOH, tetraalkylammoniumhydroxide such as, for example, tetrabutylammoniumhydroxide, especially bicylic amidine such as 1,5-diazabicyclo[4.3.0]-5-nones or 1,8-diazabicylo(5.4.0)-7-undecen, and guanidine, and, above all, tetramethylguanidine, are used.

C. Polysiloxane

The last to be considered included conventional silicone resins (compare W. Noll, Chemie und Technologie der Silicone, Verlag Chemie, Weinheim 1968; N. Auner, J. Weiss (Editors), organosilicone Chemistry, Wiley-VCH, 1997), which lead to polymer binding via condensation or hydrolysis.

To produce the compositions, organic or inorganic particles or fibers are added to the matrix systems to improve the mechanical properties. Preferred inorganic particulate fillers are amorphous spherically shaped materials based on oxides such as $ZrO_2$ and $TiO_2$ or, respectively, mixed oxides formed from $SiO_2$, $ZrO_2$ and/or $TiO_2$, nano-particulate or microfine fillers such as pyrogenic pebble acid or precipitation pebble acid as well as macro- or mini-fillers such as quartz, glass ceramic- or glass-powder with an average particle size of from 0.01 to 5 micrometers as well as roentgenopake fillers such as ytterbiumtrifluoride.

Moreover, glass fibers, whiskers, layered silicate, polyamid- or carbon-fibers can also be used.

Finally, inorganic paste can be used for the production of green or uncured bodies. In this regard, there can be used powder of glass, glass ceramics, or ceramics such as, for example, the following systems based on:

Leucite-phosphorus-silicate ($SiO_2$—$Al_2O_3$—$K_2O$—$CaO$—$P_2O_5$—F), as is described in DE 4 423 793 C1, Leucite ($SiO_2$—$Al_2O_3$—$K_2O$—)

lithiumdisilicate ($SiO_2$—$Li_2O$—) (compare DE 196 47 739 A1), corundum ($Al_2O_3$) or zirconium oxide ($ZrO_2$) as well as alkali tin silicate ($SiO_2$—$ZnO$—$Na_2O$) (compare DE 4 428 839 C2)

In this process, the powder is transformed into the moldable pastes by means of suitable conventional aid material (compare J. S. Reed, Principles of Ceramic Processing, J. Wiley & Sons, New York 1988, page 123 ff). In this regard, water, alcohol, ketone, or petroleum can be used, for example, as the solution; cellulose derivatives, polyvinyl alcohol, polyethylene glycol, paraffin, or polyvinyl butyral can be used as binders; and ethylene glycol, glycerin, dibutylphthalate, or polyethylene glycol can be used as plastifiers.

The materials for the 3-dimensional plotting can, in addition, comprise additional additives such as, for example, coloring elements (pigments or color elements), stabilizers, aroma material, microbiotic elements, softening agents, or UV absorbers.

The present invention is, of course, in no way restricted to the specific disclosure of the specification and drawings, but also encompasses any modifications within the scope of the appended claims.

What is claimed is:

1. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein the form piece is built up in layers with different types of material.

2. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein at least one of the applied layers has a selected one of a homogeneous and a heterogeneous structure.

3. A process for fabricating dental form pieces according to claim 2, wherein the at least one applied layer has a heterogeneous structure characterized by different functionalities.

4. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein at least one of the applied layers promotes at least one of a pharmaceutical effect which may include fluoride ions, a working element having an antibacterial property, and ions for assisting the remineralization of dental substances.

5. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein at least one of the layers includes fibers for enhancing the mechanical properties of the applied material.

6. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein at least one of the layers promotes release of acid neutralizing ions.

7. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein at least one of the layers has opalescence promoting properties.

8. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein at least one of the layers has the capability to be polished to a high shine.

9. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein at least one of the layers has the property of relatively less plaque retention.

10. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein at least one of the layers has a porous structure.

11. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein the dental form piece is a preprepared piece and the step of applying a material includes applying at least one of a plastic and a ceramic mass to the dental form piece to coat it.

12. A process for fabricating dental form pieces according to claim 11, wherein the dental form piece is a selected one of an implant and a prosthesis.

13. A process for fabricating dental form pieces according to claim 11, wherein the coating on the dental form piece has a bioactive property.

14. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein the step of applying a material includes applying a coating which is a selected one of a hard and a soft under composition.

15. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein the step of applying a material includes plotting in a selected one of a reactive and a non-reactive fluid medium.

16. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein the dental form piece is a ceramic core body.

17. A process for fabricating dental form pieces, comprising:

controlling a material applying device to apply onto a support body a layer of a polymerizable plastic material in an unpolymerized condition such that the applied layer can be mechanically manipulated after its application onto the support body; and applying another layer of plastic material onto the one layer of applied plastic material, all of the plastic material applied onto the support body being polymerizable into a hardened condition particularly by radiation of the plastic material with energy including light energy; and wherein the material applying device is controlled to apply a plurality of material cords as a function of the layer to be applied.

18. A process for fabricating dental form pieces according to claim 17, wherein the polymerization is performed by light energy including especially UV light energy and the polymerization is performed by the material applying device at a spacing.

19. A process for fabricating dental form pieces, comprising:

controlling a material applying device to apply onto a support body a layer of a polymerizable plastic material in an unpolymerized condition such that the applied layer can be mechanically manipulated after its application onto the support body; and applying another layer of plastic material onto the one layer of applied plastic material, all of the plastic material applied onto the support body being polymerizable into a hardened condition particularly by radiation of the plastic material with energy including light energy; and wherein the material applying device is controlled to apply cords in a three dimensional cord applying operation.

20. A process for fabricating dental form pieces, comprising:

controlling a material applying device to apply onto a support body a layer of a polymerizable plastic material in an unpolymerized condition such that the applied layer can be mechanically manipulated after its application onto the support body; and applying another layer of plastic material onto the one layer of applied plastic material, all of the plastic material applied onto the support body being polymerizable into a hardened condition particularly by radiation of the plastic material with energy including light energy; and and further comprising removing material via the material applying device in a fluid medium.

21. A process for fabricating a plastic piece according to claim 17, wherein the material applying device is controlled to apply the layers on a dry oversurface.

22. A process for fabricating dental form pieces according to claim 17, wherein at least one of the applied layers of plastic material is initially incompletely polymerized to a condition in which the layer has sufficient tractiveness for the retention of the next applied layer which is applied thereon and the completion of the polymerization of the at least one applied layer is accomplished subsequent to the application of the next applied layer.

23. A process for fabricating a dental form pieces according to claim 17, wherein the plastic material is a polymerizable dental material having up to 70 percent by weight of at least one of a polymerizable monomer and a polymerizable oligomer, 0.1 to 5 percent by weight of at least one polymerization initiator, up to 60 percent by weight of at least one filling element, and at least 20 percent by weight of a wax-like polymerizable substance.

24. A process for fabricating dental form pieces, comprising:
controlling a material applying device to apply onto a support body a layer of a hardenable plastic material in an unhardened condition such that the applied layer of plastic material can be mechanically manipulated after its application onto the support body; and
applying another layer of plastic material onto the one layer of applied plastic material, all of the plastic material applied onto the support body being hardenable into a hardened condition by at least one of polymerization, the influence of a polyaddition, and the influence of a polycondensation; and
wherein the applied layers of plastic materials are hardened by chemical reaction in a fluid medium.

25. A process for fabricating dental form pieces, comprising:
controlling a material applying device to apply onto a support body a layer of a hardenable plastic material in an unhardened condition such that the applied layer of plastic material can be mechanically manipulated after its application onto the support body; and
applying another layer of plastic material onto the one layer of applied plastic material, all of the plastic material applied onto the support body being hardenable into a hardened condition by at least one of polymerization, the influence of a polyaddition, and the influence of a polycondensation; and
wherein the material applying device is operatively connected to a one way dosing device and has a nozzle opening between 200 and 2000 micrometers.

26. A process for fabricating dental form pieces, comprising:
controlling a material applying device to apply onto a support body a layer of a hardenable plastic material in an unhardened condition such that the applied layer of plastic material can be mechanically manipulated after its application onto the support body; and
applying another layer of plastic material onto the one layer of applied plastic material, all of the plastic material applied onto the support body being hardenable into a hardened condition by at least one of polymerization, the influence of a polyaddition, and the influence of a polycondensation; and
wherein the material applying device includes a nozzle which is controlled to move in the manner of a plotter and is controlled during such movement to apply the plastic material.

27. A process for fabricating dental form pieces according to claim 26, wherein the hardening of the applied plastic material is effected by irradiation thereof by light followed by a thermal handling.

28. A process for fabricating dental form pieces, comprising:
controlling a material applying device to apply onto a support body a layer of a hardenable plastic material in an unhardened condition such that the applied layer of plastic material can be mechanically manipulated after its application onto the support body; and
applying another layer of plastic material onto the one layer of applied plastic material, all of the plastic material applied onto the support body being hardenable into a hardened condition by at least one of polymerization, the influence of a polyaddition, and the influence of a polycondensation; and
wherein the applied plastic material includes a filler element containing a high viscosity plastic material formed of at least one of a polymerizable monomer, a polymerizable oligomer, and a polymerizable polymer.

29. A process for fabricating dental form pieces according to claim 26, wherein between about 1 to 50% of the applied plastic material is at least one of a wax-like polymerizable substance in the form as desired of one of an ester of a carbon acid with a polymerizable alcohol and an ester of an alcohol with a polymerizable carbon acid derivative.

30. A process for fabricating dental form pieces for dental restoration and replacement parts, comprising:
on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and
hardening the applied material by at least one of cooling of the material, chemical reaction, polymerization with thermal handling, and polymerization by irradiation of the material by at least one of UV and visible light; and
wherein the dental form piece is used in the fabrication of a dental replacement product in a selected color.

31. A process for fabricating dental form pieces for dental restoration and replacement parts, comprising:
on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and
hardening the applied material by at least one of cooling of the material, chemical reaction, polymerization with thermal handling, and polymerization by irradiation of the material by at least one of UV and visible light; and
wherein a selected one of a tooth and a dental replacement product is fabricated by the process and the layer in the direction of the plastic material is selected such that the outermost applied layer is substantially parallel to the last layer to be applied which is in the form of a dental bloom.

32. A process for fabricating dental form pieces for dental restoration and replacement parts, comprising:
on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and
hardening the applied material by at least one of cooling of the material, chemical reaction, polymerization with thermal handling, and polymerization by irradiation of the material by at least one of UV and visible light; and
wherein the build up of the layers is selected such that the maximum length and width of the dental form piece is greater than its height.

33. A process for fabricating dental form pieces for dental restoration and replacement parts, comprising:
on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein the outermost applied layer has a greater translucent characteristic than the applied layers thereunder.

34. A process for fabricating dental form pieces for dental restoration and replacement parts, comprising:

on a selected one of a firm support and a fluid medium, applying by a three dimensional plotting technology in a layer by layer manner a material having at least one of micro cords and micro drops which includes at least one of a meltable, polymerizable, polycondensable, and polyaddable constituent element that is a selected one of an unfilled monomer, a reinforced monomer, oligomer, polymer, and a ceramic element; and hardening the applied material by at least one of cooling of the material, chemical reaction, polymerization with thermal handling, and polymerization by irradiation of the material by at least one of UV and visible light; and wherein said medium is heated by a heating means when supplied through a nozzle for application of said medium, and that said medium is polymerized in its heated state.

35. A process for fabricating dental form pieces according to claim 1 wherein the form piece is built up in layers with different types of material to produce a body formed in a layer by layer manner during three dimensional plotting technique during which polymerization is used at least partially to effect hardening of the material applied during the three dimensional plotting technique.

* * * * *

UNITED STATES PATENT AND TRADEMARK OFFICE
CERTIFICATE OF CORRECTION

PATENT NO. : 6,939,489 B2
DATED : September 6, 2005
INVENTOR(S) : Norbert Moszner et al.

It is certified that error appears in the above-identified patent and that said Letters Patent is hereby corrected as shown below:

Column 16,
Line 47, delete "and";
Line 49, "a plastic piece" should be -- dental form pieces --;
Line 49, delete "a" (second occurrence).

Signed and Sealed this

Twentieth Day of December, 2005

JON W. DUDAS
*Director of the United States Patent and Trademark Office*